(12) United States Patent
Butler et al.

(10) Patent No.: US 8,177,813 B2
(45) Date of Patent: May 15, 2012

(54) EXPANDABLE SPINAL SPACER

(75) Inventors: Michael S. Butler, St. Charles, IL (US); Brian D. Hartsell, Aurora, IL (US)

(73) Assignee: Life Spine, Inc., Hoffman Estates, IL (US)

( * ) Notice: Subject to any disclaimer, the term of this patent is extended or adjusted under 35 U.S.C. 154(b) by 673 days.

(21) Appl. No.: 12/234,634

(22) Filed: Sep. 20, 2008

(65) Prior Publication Data
US 2009/0082808 A1    Mar. 26, 2009

Related U.S. Application Data

(60) Provisional application No. 60/994,608, filed on Sep. 20, 2007.

(51) Int. Cl.
*A61B 17/70* (2006.01)
(52) U.S. Cl. ........................ 606/249; 606/262
(58) Field of Classification Search .............. 606/90, 606/92–94, 105, 246–249, 261
See application file for complete search history.

(56) References Cited

U.S. PATENT DOCUMENTS

| | | | | |
|---|---|---|---|---|
| 4,462,394 A * | 7/1984 | Jacobs | | 606/94 |
| 5,549,679 A * | 8/1996 | Kuslich | | 623/17.12 |
| 5,702,454 A * | 12/1997 | Baumgartner | | 128/898 |
| 6,066,154 A * | 5/2000 | Reiley et al. | | 606/192 |
| 6,464,727 B1 * | 10/2002 | Sharkey et al. | | 623/17.16 |
| 6,616,673 B1 * | 9/2003 | Stone et al. | | 606/105 |
| 6,936,072 B2 * | 8/2005 | Lambrecht et al. | | 623/17.16 |
| 7,335,203 B2 * | 2/2008 | Winslow et al. | | 606/249 |
| 7,857,856 B2 * | 12/2010 | Trieu | | 623/17.16 |
| 2002/0123750 A1 * | 9/2002 | Eisermann et al. | | 606/69 |
| 2002/0156482 A1 * | 10/2002 | Scribner et al. | | 606/92 |
| 2003/0004574 A1 * | 1/2003 | Ferree | | 623/17.12 |
| 2004/0249379 A1 | 12/2004 | Winslow et al. | | |
| 2005/0261768 A1 * | 11/2005 | Trieu | | 623/17.11 |
| 2006/0085074 A1 * | 4/2006 | Raiszadeh | | 623/17.12 |
| 2006/0122620 A1 | 6/2006 | Kim | | |
| 2007/0093830 A1 | 4/2007 | Zucherman et al. | | |
| 2007/0142915 A1 | 6/2007 | Altarac et al. | | |
| 2007/0161991 A1 | 7/2007 | Altarac et al. | | |
| 2008/0058934 A1 * | 3/2008 | Malandain et al. | | 623/17.11 |

FOREIGN PATENT DOCUMENTS

WO    2006089085 A2    8/2006

* cited by examiner

*Primary Examiner* — Eduardo C Robert
*Assistant Examiner* — Jerry Cumberledge
(74) *Attorney, Agent, or Firm* — Foley & Lardner LLP

(57) ABSTRACT

A spinal spacer or stenotic device is expandable, inflated and/or filled in situ or ex vivo through the addition of a biocompatible fill material into the spinal implant once inserted or implanted in like manner to an angioplasty bag. Once implanted, expansion or inflation of the present expandable spinal spacer distracts the spine (creates spacing). The present expandable spinal spacer can operate as an interspinous, interspinous process, or intralaminar spinal spacer. In general the present expandable spinal space creates and/or maintains spacing between vertebrae or components of vertebrae. The present expandable spinal spacer is formed of a generally pliable biocompatible material that is collapsible and expandable/fillable. Preferably, but not necessarily, the biocompatible material is a mesh or weave type material, although other materials may be used.

3 Claims, 5 Drawing Sheets

EXPANDABLE SPINAL SPACER

RELATED APPLICATIONS

This patent application claims the benefit of and/or priority to U.S. Provisional Patent Application Ser. No. 60/994,608 filed Sep. 20, 2007, entitled "Expandable Spinal Spacer" the entire contents of which is specifically incorporated herein by this reference.

BACKGROUND OF THE INVENTION

1. Field of the Invention

The present invention relates to devices for the spine and, more particularly, to devices for creating and/or maintaining spacing between vertebrae.

2. Background Information

As we age various changes can occur in the body. For instance, the ligaments of the spine can thicken and calcify (i.e. harden from deposits of calcium), bone and joints may enlarge, bone spurs called osteophytes may form, spinal discs may collapse and bulge (i.e. herniate) or one vertebra may slip over another (spondylolisthesis). Any one or these conditions and/or others can cause what is known as lumbar spinal stenosis. Lumbar spinal stenosis is a narrowing of the bony spinal canal. While some people are born with this condition, most often spinal stenosis is the result of one of the above-identified degenerative conditions that develop in mainly the middle-aged and elderly population.

In this regard, spinal stenosis may be considered as the gradual result of aging and "wear and tear" on the spine from everyday activities. Such degenerative or age-related changes in our bodies can lead to compression of nerves (i.e. pressure on the nerves that can cause pain and/or damage). Symptoms of lumbar spinal stenosis include leg pain ("pins and needles") that can limit standing, walking, self-supporting daily activities, work social and recreational pursuits. Lack of activity because of lumbar spinal stenosis may lead to obesity, depression and general physical deterioration.

Once diagnosed with lumbar spinal stenosis the doctor will usually try non-surgical treatments first. Such treatments may include anti-inflammatory medications (orally or by injection) to reduce associated swelling or analgesic drugs to control pain. Physical therapy may be prescribed with goals of improving ones strength, endurance and flexibility so that you can maintain or resume a more normal lifestyle. Spinal injections such as an epidural injection of cortisone may also be used. Such non-surgical treatments do not correct the spinal canal narrowing of lumbar spinal stenosis itself but may provide long-lasting pain control and improved life function without requiring a more invasive treatment. However, as a last resort for those patients who don't respond to non-surgical treatments, surgery will be advised.

Lumbar spinal stenosis is the most common reason for back surgery in people over the age of 50 in the United States. In 1995 it was reported that 1.2 million physician office visits were related to symptoms of lumbar spinal stenosis and this number may be closer to 2 million today. While there are various non-surgical treatments for lumbar spinal stenosis, a surgical procedure known as a laminectomy may be performed in order to reduce or eliminate the symptoms of lumbar spinal stenosis. A laminectomy or lumbar decompression surgery has the goal of opening up the bony canal to improve available space for the spinal nerves.

It is estimated that there were more than 125,000 laminectomy procedures performed for lumbar spinal stenosis in 2003 alone and this number is most likely more today. The financial impact in terms of health care dollars and lost work hours reached billions of dollars each year in this country. Rapidly expanding numbers of people over the age of 50 represent a global health care challenge without precedent and lumbosacral pain is a significant health care issue. In 2000, the number of persons aged 60 years or older was estimated at 605 million. That number is project to grow to almost 2 billion by 2050 when the population of older persons will be larger than the population of children (0-14 years) for the first time in human history.

As indicated, a decompression laminectomy is usually a last resort for treating spinal stenosis. This is because a decompression laminectomy is an invasive surgical procedure.

It would thus be desirable to provide a surgical treatment for spinal stenosis that is less invasive than a decompression laminectomy.

It would also be desirable to provide a device for treating spinal stenosis.

It would moreover be desirable to provide a device for creating and/or maintaining space or spacing between vertebrae.

SUMMARY OF THE INVENTION

The present invention is a spinal spacer or stenotic device that is expandable, inflated and/or filled in situ and/or ex vivo. The present expandable spinal spacer is inserted or implanted in like manner to an angioplasty bag and is expanded and/or filled in situ through the addition of bone cement or other biologic into the spinal implant. Once implanted, expansion of the present expandable spinal spacer distracts the spine thereby alleviating spinal stenosis. The present expandable spinal spacer can operate as an interspinous, interspinous process or intralaminar spinal spacer. In general the present expandable spinal space creates and/or maintains spacing between vertebrae or components of vertebrae.

The present expandable spinal spacer is formed of a generally pliable biocompatible material that is collapsible and expandable. Preferably, but not necessarily, the biocompatible material is a mesh or weave type material, although other materials may be used. Expansion of the present spinal implant is achieved through the addition of a filler material that may be any type of biocompatible material such as a biologic material, inert material, or the like once the spinal implant has been introduced and properly situated on the spine.

In one form, the present expandable spinal spacer is formed of an expandable body defining an internal, expandable/fillable cavity. One or more segments, portions, sections or arms extend laterally from the body. Each lateral segment defines an internal cavity that is in communication with the internal cavity of the body. Each lateral segment is formed of an expandable member defining an internal, expandable/fillable cavity that is in communication with the internal cavity of the body. An end member is provided at the end of each lateral segment that is distal the body and defines an internal, expandable/fillable cavity that is in communication with the internal cavity of the lateral segment. The end member has an increasing diameter opposite the connection point to the lateral segment.

In one form, the expandable body may be tubular or define a tube and therefore provide an internal, expandable/fillable tubular cavity. Likewise, each lateral segment is defined by a tubular arm to therefore provide an internal, expandable/fillable tubular cavity. The end member may be fashioned as a bulb or rounded portion thereby defining an internal, expandable/fillable rounded or bulbous cavity that is in communication with the internal cavity of the tubular lateral segment. Other configurations for these structures are contemplated such as for the bulb.

The present expandable spinal spacer may be a single level device or a multi-level device. In one form, the present expandable spinal spacer is formed of a poly or polymer mesh or weave bag that is implanted collapsed and then pressurized with the bone cement or other biologic. Other biocompatible materials may be used for the present expandable spinal spacer and are contemplated.

Various portions, sections or segments of the present expandable spinal spacer may be configured to expand to different sizes. The lateral segments may be the same size as the tubular body or may be narrow or large in comparison. In this manner, various portions of the present expandable spinal spacer are allowed to expand more than other parts of the spacer.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

Like reference numerals indicate the same or similar parts throughout the several figures.

A thorough discussion of the features, functions and/or configurations of the components depicted in the various figures will now be presented. It should be appreciated that not all of the features of the components of the figures are necessarily described. Some of these non discussed features as well as discussed features are inherent from the figures. Other non discussed features may be inherent in component geometry and/or configuration.

DETAILED DESCRIPTION OF AN EMBODIMENT OF THE INVENTION

Figure 1:
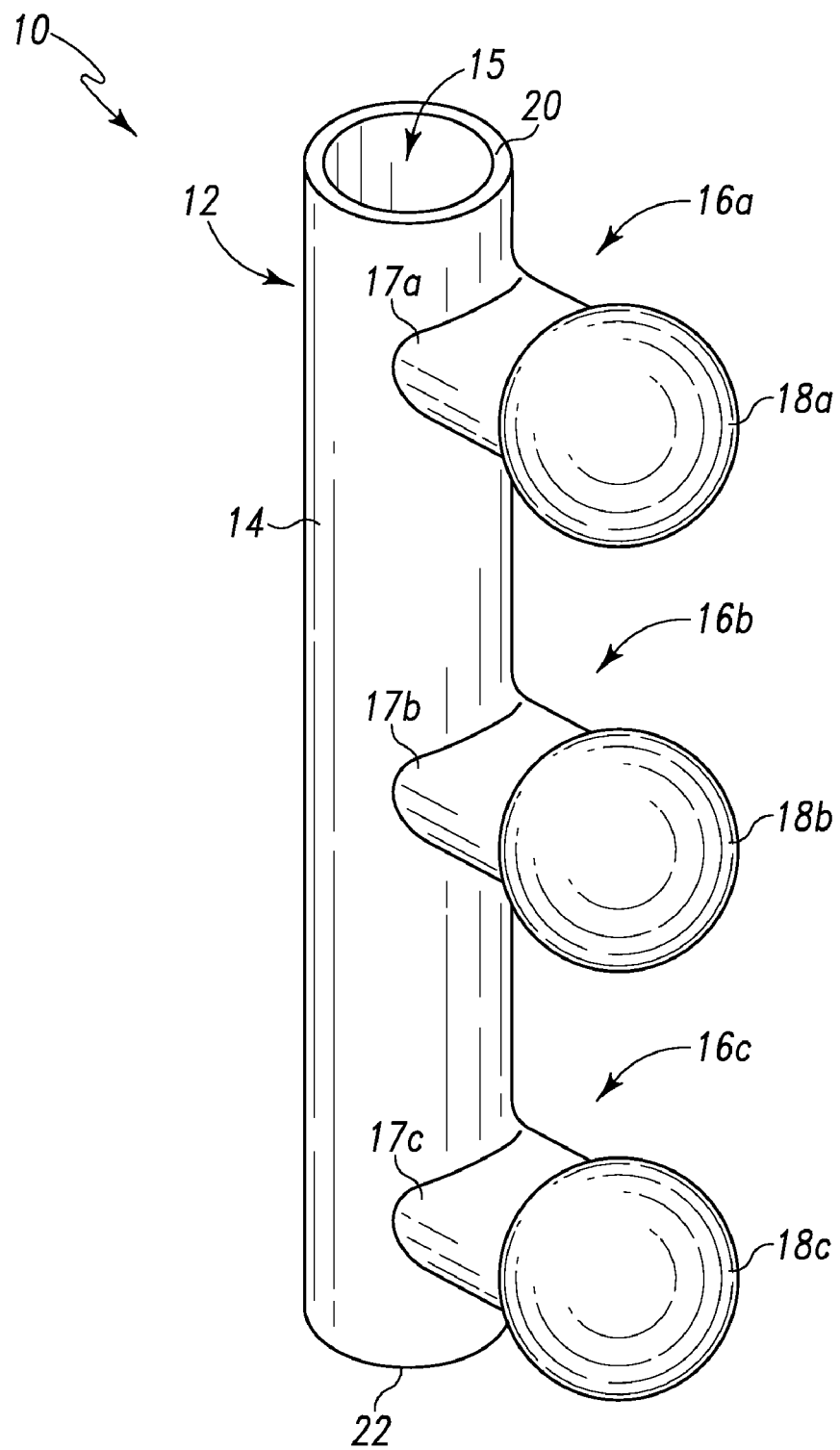
FIG. 1 is a front side perspective view of an embodiment of the present expandable spinal spacer in an expanded state.
Figure 2:
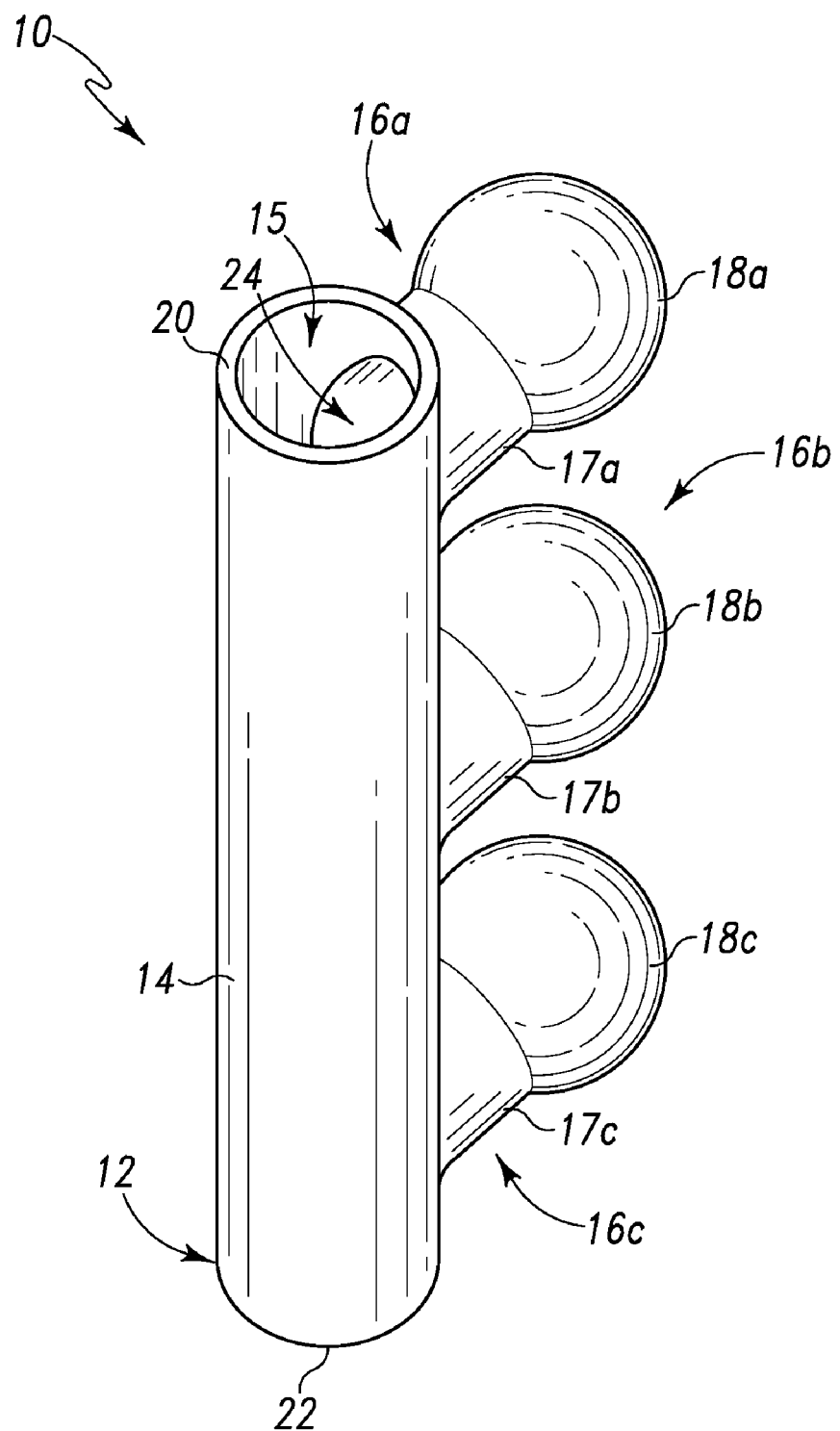
FIG. 2 is a rear side perspective view of the expandable spinal spacer of FIG. 1, the expandable spinal spacer in an expanded state.
Figure 3:
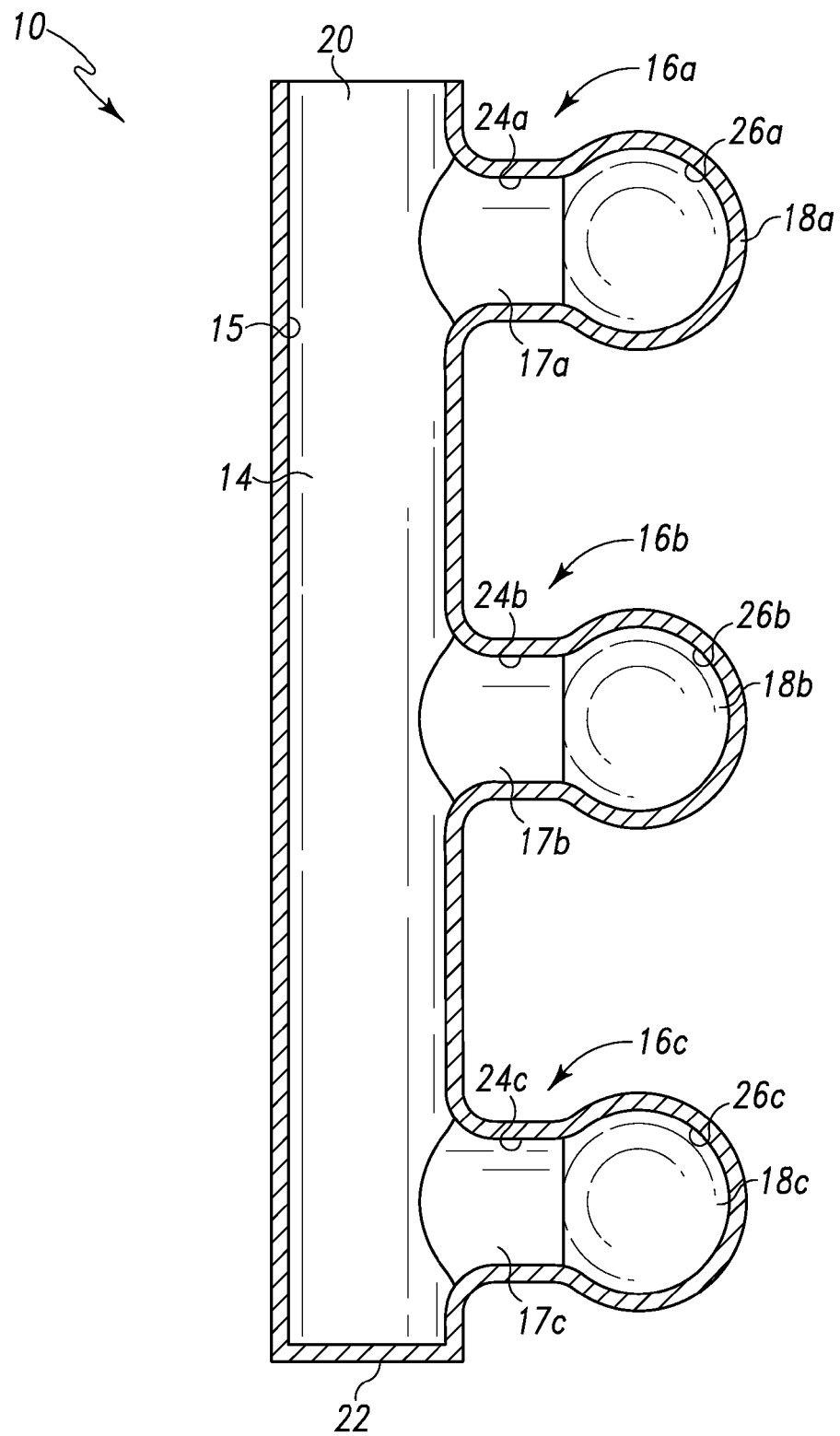
FIG. 3 is a side view of the expandable spinal spacer of FIG. 1 particularly showing internal cavities thereof.

Referring to FIGS. 1-3 there is depicted an exemplary embodiment of an expandable spinal spacer, generally designated 10, fashioned in accordance with the present principles. The expandable spinal spacer 10 is fashioned from an expandable and/or pliant biocompatible material such as a poly/polymer mesh but may be fashioned from other expandable biocompatible materials such as other mesh or weave type materials. Solid but pliant biocompatible materials may also be used. As such, the present expandable spinal spacer 10 may be considered a configured bag able to define a collapsed state and an expanded or filled state. The expandable spinal spacer 10 is shown in an expanded or filled state.

It should be appreciated that the present expandable spinal spacer defines an expandable main body and one or more expandable transverse segments with each transverse segment having an end member that is larger in size (e.g. diameter) than the transverse segment. Additionally and/or alternatively, each lateral segment may increase in size from the connection point to the main body to the expandable end member. The body, lateral segments and end members are each hollow or define an internal cavity for receipt of a biocompatible fill material. The various components may be fashioned in various configurations. A tubular version is shown but is not limiting to the possible configurations of the present invention.

The expandable spinal spacer 10 has an expandable body that is fashioned as tubular or a tube 14 defining an internal tubular cavity 15. The tubular cavity 15 is open at end 20 and may or may not be open at end 22 thereof. In the embodiment shown, the expandable spinal spacer 10 has three (3) segments, portions or sections 16 that laterally extend from the tubular body 14 and separately labeled 16a, 16b and 16c. It should be appreciated that the expandable spinal spacer 10 may have more or less lateral segments as desired in order to make the expandable spinal spacer a single level or multi-level spinal spacer. Each lateral segment 16 is defined by a tubular arm 17 (separately labeled 17a, 17b and 17c corresponding to lateral segments 16a, 16b and 16c) that laterally extends from the tubular body 14. Each tubular arm 17 terminates in a rounded end, ball or bulb 18 (separately labeled 18a, 18b and 18c corresponding to lateral segments 16a, 16b and 16c). Each tubular arm 17 may terminate in an end having a different geometry or configuration as desired.

It should be appreciated that the body, lateral segments and ends may be different configurations while keeping within the present principles. Therefore, while the body is shown as a tubular segment, and the lateral segments are shown as tubular with rounded or bulbous ends, the configuration and/or geometry of the lateral segments and the ends may vary. Thus, the lateral segments may be formed of an arm of a non-tubular configuration while the ends thereof may not be rounded.

As best depicted in FIG. 3, each lateral segment 16 (here, lateral segments 16a, 16b and 16c) is hollow or has a cavity therein that is in communication with the tubular cavity 15 of the tubular body 14. Particularly the tubular arm 17 has a hollow or cavity 24 (separately labeled 24a, 24b and 24c corresponding to lateral segments 16a, 16b and 16c) that is in communication with the internal tubular cavity 15 while the rounded end 18 has a hollow or cavity 26 (separately labeled 26a, 26b and 26c corresponding to lateral segments 16a, 16b and 16c) that is in communication with the cavity 24.

Bone cement or other biologic, saline or any other biocompatible material is used as a fill and thus is inserted into the tubular cavity 15 flows into the segments 16 via the cavities 24, 26 thereby expanding or filling the segments and thus the spinal spacer 10 (in situ—i.e. once implanted). Various portions, sections or segments of the present expandable spinal spacer 10 may be configured to expand or fill to different sizes. The lateral segments may be the same size as the tubular body or may be narrow or large in comparison. In this manner, various portions of the present expandable spinal spacer may be allowed to expand or fill more than other parts of the spacer.

It should be appreciated that the expandable spinal spacer 10 may come in various sizes/dimensions to accommodate various spinal anatomies as well as for create, maintain and/or provide a desired spacing between vertebrae.

The present expandable spinal spacer 10 is implanted in the same manner as an angioplasty bag: through an incision made in the patient proximate the area of implantation. The expandable spinal spacer 10 is implanted and filled with the biologic material (e.g. bone cement) whereby adjacent vertebrae are then distracted by the expansion or filling of the expandable spinal spacer. The rounded ends or bulbs 18 hold the spinal spacer 10 in place once expanded within the particular vertebral area. The bulbs 18 also act to prevent rotation once installed.

Figure 4:
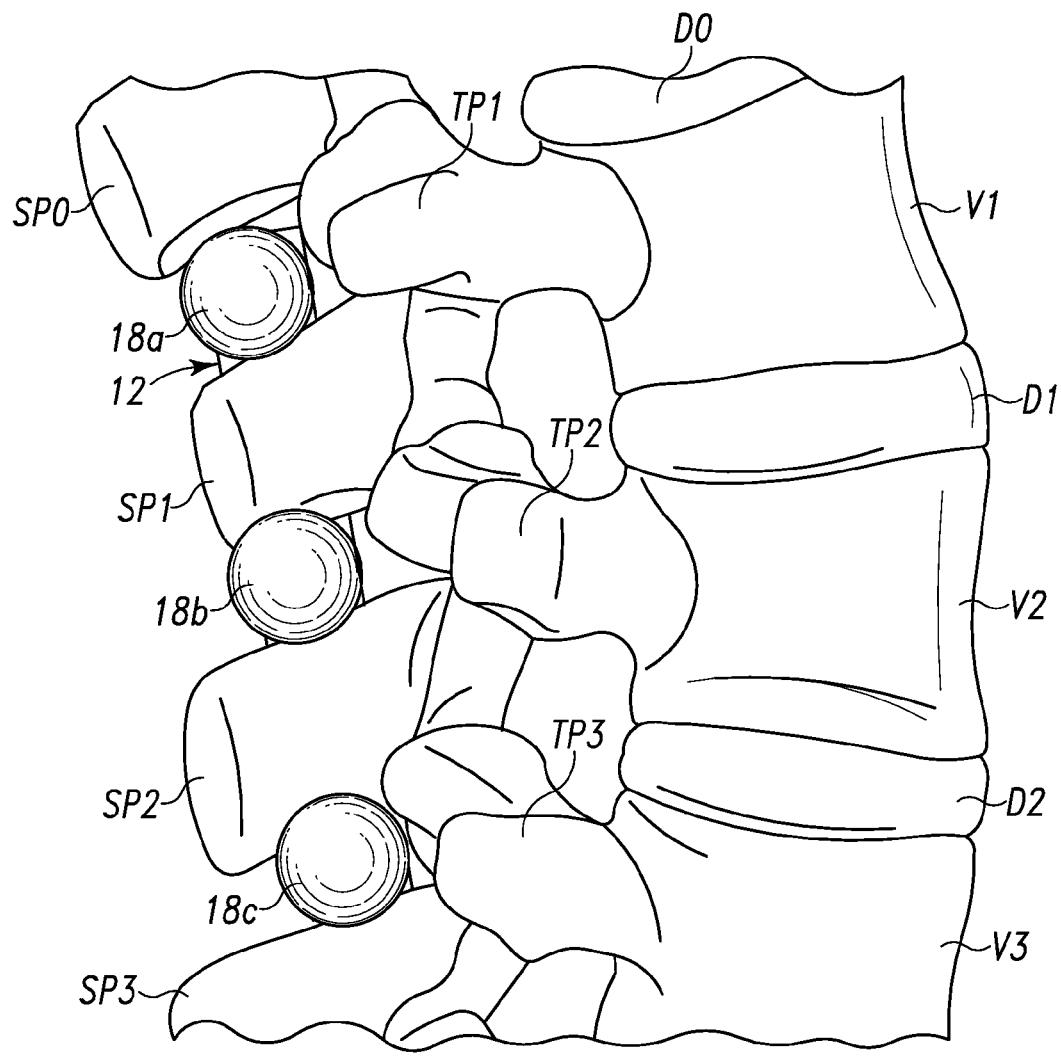
FIG. 4 is a lateral view of a portion of a lumbar portion of the spine with the present expandable spinal spacer situated thereon, the present expandable spinal spacer being used as a spinous process spacer.
Figure 5:
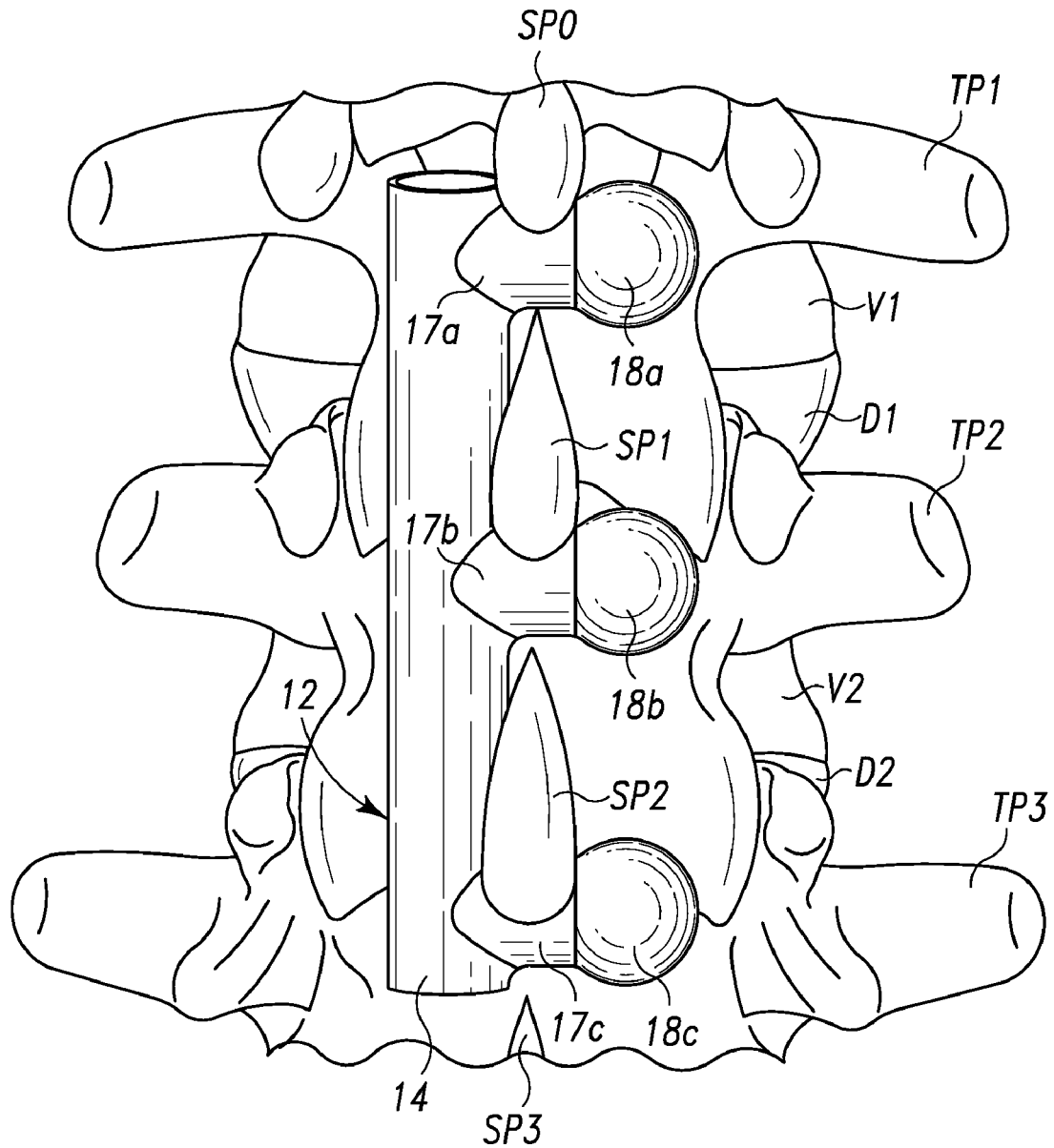
FIG. 5 is a posterior view of the portion of the lumbar spine of FIG. 4 showing the present expandable spinal spacer situated thereon.

FIGS. 4 and 5 depict the present expandable spinal spacer implanted into the lumbar portion of the spine as an intraspinous process (i.e. situated between spinous processes). Particularly, a three (3) vertebrae portion of the lumbar portion of a spine is shown, the vertebrae labeled V1, V2 and V3 with disc D1 between vertebrae V1 and V2 while disc D2 is between vertebrae V2 and V3. The transverse processes of the three vertebrae are labeled beginning with the letters "TP" while the spinous processes thereof are labeled beginning with the letters "SP." The present expandable spinal spacer 10 is shown implanted adjacent (laterally against) the spinous processes SP1, SP2 and SP3 of respective vertebrae V1, V2 and V3.

Particularly, the tubular body 12 is situated laterally adjacent the spinous processes SP1, SP2 and SP3 while the arm 17a extends between and supports spinous processes SP0 (of a vertebra V0 not shown) and SP1 of vertebra V1, arm 17b extends between and supports spinous processes SP1 of vertebra and SP2 of the vertebra V2, and arm 17c extends between and supports spinous processes SP2 and SP3. The bulbs 18a, 18b and 18c are thus situated on the lateral side of the spinous processes opposite the body 12 of the expandable spine implant 10. Particularly, bulb 18a is situated laterally adjacent spinous processes SP0 and SP1, bulb 18b is situated laterally adjacent spinous processes SP1 and SP2, while bulb 18c is situated laterally adjacent spinous processes SP2 and SP3. The device may be placed in or about the spine, including intralaminar, intraspinous process, intra transverse process, and intra discal.

While the invention has been illustrated and described in detail in the drawings and foregoing description, the same is to be considered as illustrative and not restrictive in character, it being understood that only a preferred embodiment has been shown and described and that all changes and/or modifications that come within the spirit of the invention are desired to be protected.

What is claimed is:

1. A spinal spacer comprising:
   a hollow, elongated tubular body defining a body interior;
   a plurality of hollow tubular arms each one of which extends generally parallel to each other and generally perpendicular from the hollow, elongated tubular body and defines an arm interior; and
   a hollow end member situated on an end of each one of the plurality of hollow tubular arms distal the hollow elongated tubular body, each one of the plurality of hollow end members defining an end member interior that is in communication with the its respective arm interior;
   the hollow elongated tubular body, hollow tubular arms and hollow end members defining a collapsed state during which the spinal spacer may be implanted relative to a spine, and an expanded state after the hollow elongated tubular body, the hollow tubular arms and the hollow end members are filled with a substance after being implanted relative to the spine;
   wherein each hollow tubular arm has an outer dimension and each hollow end member has an outer dimension, the outer dimension of the hollow end member being larger than the outer dimension of the respective hollow arm when the hollow arms and hollow end members are in the expanded state.

2. The spinal spacer of claim 1, wherein each one of the plurality of hollow end members is bulbous.

3. The spinal spacer of claim 1, wherein the hollow elongated tubular body, hollow tubular arms and hollow end members are formed of a collapsible biocompatible material comprising a poly mesh.

\* \* \* \* \*